United States Patent
Rando

Patent Number: 5,202,456
Date of Patent: Apr. 13, 1993

[54] COMPOUNDS FOR INHIBITION OF PROTEIN METHYLATION

[75] Inventor: Robert R. Rando, Newton Center, Mass.

[73] Assignee: The President and Fellows of Harvard College, Cambridge, Mass.

[21] Appl. No.: 685,597

[22] Filed: Apr. 15, 1991

[51] Int. Cl.$^5$ .................. C07C 255/00; C07C 321/00; C07C 53/00; C07C 249/00

[52] U.S. Cl. .................................. 558/438; 560/152; 562/23; 562/512; 562/556; 562/557; 562/581; 564/268; 568/943

[58] Field of Search ............... 562/598, 557, 556, 581, 562/23, 512; 260/401; 560/149, 150, 152; 558/437, 438; 554/45, 46, 49; 568/943; 564/268

[56] References Cited

PUBLICATIONS

Hancock et al. Cell, 57:1167 (1989).
Gutierrez et al. Embo, J. 8:1093 (1989).
Willumsen et al. Embo, J. 3:2581 (1989).
PNAS 87:7673 (1990) Lai et al.
Farnsworth et al. J. B. C. 264:20422 1989.
Maltese et al. J. Cell Physiol. 125:540 1985.
Sinensky et al. PNAS 82:3257 1985.
Beck et al. J. Cell Bio. 107:1307 1988.
Hancock et al. Embo, J. 10:641 (1991).
Anderegg et al. J. B. C. 263:18236 (1988).
Chelsky et al. J. B. C. 262:20422 (1989).
Vorburger et al. Embo, J. 8:4007 (1989).

*Primary Examiner*—Paul J. Killos
*Assistant Examiner*—Joseph M. Conrad

[57] ABSTRACT

The invention features a compound of the formula

W-Y-Q-Z or W-Y-Z wherein
W is a farnesyl group, a geranylgeranyl group, a substituted farnesyl group or a substituted geranylgeranyl group;

$$Y \text{ is } -S-, -O-, -Se-, -\overset{O}{\underset{\|}{S}}-,$$

$$-\overset{N}{\underset{\|}{\underset{O}{S}}}-, -\overset{O}{\underset{\|}{\underset{O}{S}}}-, -\overset{O}{\underset{\|}{Se}}-, \text{ or } -\overset{O}{\underset{\|}{\underset{O}{Se}}}-;$$

$$Q \text{ is } \begin{matrix} T_{1'} & & T_{n'} \\ | & & | \\ C_1 & \cdots & C_n \\ | & & | \\ T_{1''} & & T_{n''} \end{matrix}$$

wherein n=1, 2, 3, 4, 5, or 6; each of $T_{1'} \ldots T_{n'}$ and $T_{1''} \ldots T_{n''}$ is independently: Fl, Br, —NHCOCH$_3$, —NH$_2$, a peptide, an alkane group, an alkene group, an polyethyleneglycol group, a saturated fatty acid, an unsaturated fatty acid, a monosaccharide, or a disaccharide; and Z is —COOH or salts or esters thereof, —CONH$_2$, —NO$_2$, —PO$_3$ or salts or esters thereof, —C N, or —SO$_3$ or salts or esters thereof, provided that when W is farnesyl, Y is —S—, n=2, and either $T_{2'}$ or $T_{2''}$ is —NHCOCH$_3$, then Z is not —COOH.

The compounds of the invention are capable of interfering with enzymatic methylation of a peptide having the carboxyl-terminal motif —CAAX wherein C=cysteine, A=aliphatic amino acid, and X=any amino acid.

22 Claims, 2 Drawing Sheets

COMPOUNDS FOR INHIBITION OF PROTEIN METHYLATION

BACKGROUND OF THE INVENTION

This invention was supported under NIH Grant EY-03624 and the U.S. Government has certain rights to the invention.

This invention relates to controlling neoplastic cell growth.

Activated ras genes have been associated with a number of human cancers. An activated ras gene, H-ras-1, was the first non-viral oncogene discovered. Several other human ras proto-onco genes have subsequently been identified including H-ras-2, K-ras-1, K-ras-2, and N-ras. For each of these ras genes several activated mutant forms have been identified. Activated K-ras genes have been detected in pre-malignant neoplasms of the human colon and in human preleukemia.

The ras proteins, and ras-like proteins, as well as other proteins such as signal transducing G proteins, have a conserved carboxyl-terminal —CAAX motif (C=cysteine, A= aliphatic amino acid, and X=any amino acid). This motif is involved in a series of post-translational modifications including polyisoprenylation, carboxyl-terminal proteolysis, and carboxyl-methylation.

A number of ras-related small GTP binding proteins including R-ras, RAS2, rap-2, and pho B also have a carboxyl-terminal —CAAX motif, and it has been suggested that these proteins may also be post-translationally modified in the same manner (Hancock et al., *Cell* 57:1167, 1989). Among ras proteins, H-ras, N-ras (Gutierrez et al., *EMBO J.*, 8:1093, 1989) and K-ras (Hancock et al., *Cell*, 57:1167, 1989) undergo polyisoprenylation, carboxyl-terminal proteolysis and carboxyl-methylation. Inhibition of these modifications by mutation of Cys$^{186}$ to Ser blocks both membrane localization of ras gene product and transformation of the cell (Willumsen et al., *EMBO J.* 3:2581; Gutierrez et al., *EMBO J.* 8:1093, 1989).

Analysis of in vitro translated K-ras demonstrated that farnesylated, non-proteolysed, non-methylated K-ras associates inefficiently with cell membranes. Removal of the carboxyl-terminal three amino acids of this K-ras product increases membrane binding 2-fold, and methylation of the K-ras product increases membrane binding another two-fold (Hancock et al., *EMBO J.* 10:641, 1991).

A number of other proteins which have a carboxyl-terminal —CAAX motif including the γ-subunit of transducin (Lai et al., *Proc. Natl. Acad. Sci.* USA, 87:7673, 1990), yeast mating factor mata (Anderegg et al., *J. Biol. Chem.*, 263:18236, 1988), and nuclear lamin B (Chelsky et al., *J. Bio. Chem.*, 262:4303, 1987; Farnsworth et al., *J. Biol. Chem.*, 264:20422, 1989; Vorburger et al., *EMBO J.*, 8:4007, 1989) have also been shown to undergo polyisoprenylation, carboxyl-terminal proteolysis, and carboxyl-methylation.

Mevinolin inhibits cellular synthesis of mevalonic acid; this leads to depletion of polyisoprenoids and is expected to interfere with polyisoprenylation reactions. Mevinolin affects post-translational processing of ras proteins and interferes with ras membrane localization (Hancock et al., *Cell* 57:1167, 1989). In addition, cells treated with mevinolin are blocked in cell growth in the G1 phase and the G2/M phase (Maltese et al., *J. Cell Physiol.* 125:540, 1985). It has been proposed that this growth arrest, which is associated with the inhibition of mevalonate incorporation into polypeptides but not other isoprenoid derivatives such as cholesterol (Sinensky et al., *Proc. Natl. Acad. Sci.* USA, 82:3257, 1985), is caused by disruption of nuclear lamin B function (Beck et al., *J. Cell. Biol.*, 107:1307, 1988). The observation that mevinolin interferes with post-translational modification of the ras gene product combined with involvement of activated ras genes in human malignancies has led to the suggestion that mevinolin or derivatives of mevinolin may prove to be novel cytotoxic/static agents or even a starting point for the development of an anti-ras drug (Hancock et al., *Cell* 57;1167, 1989).

SUMMARY OF THE INVENTION

In general, the invention features certain novel compounds which inhibit methylation of proteins having a carboxyl-terminal —CAAX motif (C=cysteine, A=aliphatic amino acid, and X=any amino acid).

In general the invention features compounds having the formula W-Y-Q-Z or W-Y-Z wherein W is a farnesyl group, a geranylgeranyl group, a substituted farnesyl group or a substituted geranylgeranyl group; Y is:

where n=1, 2, 3, 4, 5, or 6. It is understood that $C_1 \ldots C_n$ represents 1 to 6 carbons and that when there are two or more carbons, they are connected in a linear chain by covalent bonds. The covalent bonds may be single, double or triple bonds. When there are three or more carbons the bonds do not all have to be of the same type. For example, $C_1$ may be attached to $C_2$ by a single bond, and $C_2$ may be attached to $C_3$ by a double bond. When double or triple bonds are present, two or more of $T_{1'} \ldots T_{n'}$ and $T_{1''} \ldots T_{n''}$ are eliminated. Each of $T_{1'} \ldots T_{n'}$ and $T_{1''} \ldots T_{n''}$ is independently: H, Fl, Br, —NHCOCH$_3$, —NH$_2$, a peptide (preferably linked to $C_n$ by an amide bond; preferably of 10 or fewer amino acids), an alkane group (preferably linked to $C_n$ by an amide bond; preferably of 20 or fewer carbons), an alkene group (preferably linked to $C_n$ by an amide bond; preferably of 20 or fewer carbons), an polyethyleneglycol group (preferably linked to $C_n$ by an amide bond), a saturated fatty acid (preferably linked to $C_n$ by an amide bond; preferably of 20 or fewer carbons), or an unsaturated fatty acid (preferably linked to $C_n$ through an amide bond; preferably of 20 or fewer carbons), a monosaccharide (preferably attached to $C_n$ through carbon or oxygen), or a disaccharide (preferably attached to $C_n$ through carbon or oxygen); and Z is —COOH or salts or esters (preferably salts or esters (preferably methyl, ethyl, or propyl) thereof, —C N, or —SO$_3$ or salts or esters (preferably methyl, ethyl, or propyl) thereof. Esters of —COOH, —PO$_3$, or —SO$_3$ are preferred to the free acid because they are more readily taken up by cells. Many cells have esterases which can regenerate the free acid, which is in some cases preferred for inhibition of methylation.

The compounds according to the invention are capable of inhibiting methylation of a protein having a carboxyl terminal —CAAX motif, wherein C=cysteine, A=any aliphatic amino acid, and X=any amino acid.

Regarding the farnesyl and geranylgeranyl moieties, hydrogen may generally be replaced by fluorine and a methyl group may generally be replaced by a bromine. Accordingly, "substituted farnesyl group" means a farnesyl moiety in which one or more hydrogens have been replaced by fluorine or one or more methyl groups have been replaced by a bromine, and "substituted geranylgeranyl group" means a geranylgeranyl moiety in which one or more hydrogens have been replaced by fluorine or one or more methyl groups have been replaced by bromine. In the first aspect of the invention, there is a caveat that excludes the AFC compound described below.

In various preferred embodiments, Y is a sulfoxide and n=1 or 2; n=1; the compound is a compound depicted in Table 1; the peptide is the γ subunit of transducin.

In a related aspect the invention features a therapeutic composition which includes the above-described compound capable of inhibiting methylation of a protein having a carboxyl terminal —CAAX motif.

In a related aspect the invention features a method for controlling neoplastic cell growth in a patient. The method includes administering to the patient the a therapeutic composition comprising the above described compound (without the final caveat).

As explained below, the methylation of —CAAX proteins is reversible. Because the methylation reaction is reversible in vivo and because it is important for efficient membrane binding of ras, it is a useful target for blocking the pathogenic action of ras proteins.

Other features and advantages of the invention will be apparent from the following description of the preferred embodiments and from the claims.

BRIEF DESCRIPTION OF THE DRAWINGS

The drawings are first briefly described.

DETAILED DESCRIPTION OF THE INVENTION

Compounds according to the invention are characterized by the ability to reduce methylation of a protein having a carboxyl-terminal —CAAX motif (e.g. the ras gene product). The methylation reaction which is inhibited is part of a series of post-translational modifications involving the —CAAX motif. These modifications include polyisoprenylation of the cysteine of the —CAAX motif (on the sulfur), proteolysis of the carboxyl-terminal three amino acids (—AAX) and methylation of the carboxyl group of cysteine.

The compounds of the invention may be either classic competitive inhibitors or, in a less preferred alternative, an enzyme substrate that has a Km low enough to cause an effective reduction in methylation of the normal protein substrate (e.g.,the ras gene product). Standard assays may be used to determine Km for substrates and Ki for inhibitors. Generally preferred compounds have small values of Ki or Km. The values of Ki and Km are calculated from kinetic assays by conventional means (Fersht, Enzyme Structure and Mechanism, W. H. Freeman and Co., New York, 1984). Examples are provided below to illustrate suitable assays, and are not intended to limit the invention.

One suitable assay of methylation functions uses bovine retinal rod outer segment (ROS) methyltransferase and a natural substrate, transducin. Interestingly, this system is a useful surrogate for the ras gene product methylation system that is of primary concern. Accordingly, one preferred class of compounds according to the invention includes inhibitors of transducin methylation. Another suitable assay uses N-acetyl-S-farnesylcysteine as a substrate for ROS methyltransferase.

Yet another suitable assay uses cultures of cells harboring an activated ras gene to measure the ability of candidate compounds to inhibit cell proliferation.

Figure 1:
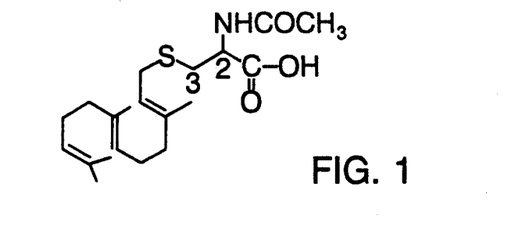
FIG. 1 is schematic drawing of the structure of N-acetyl-S-farnesylcysteine. The number 2 carbon is indicated as is the number 3 carbon.
Figure 2A:
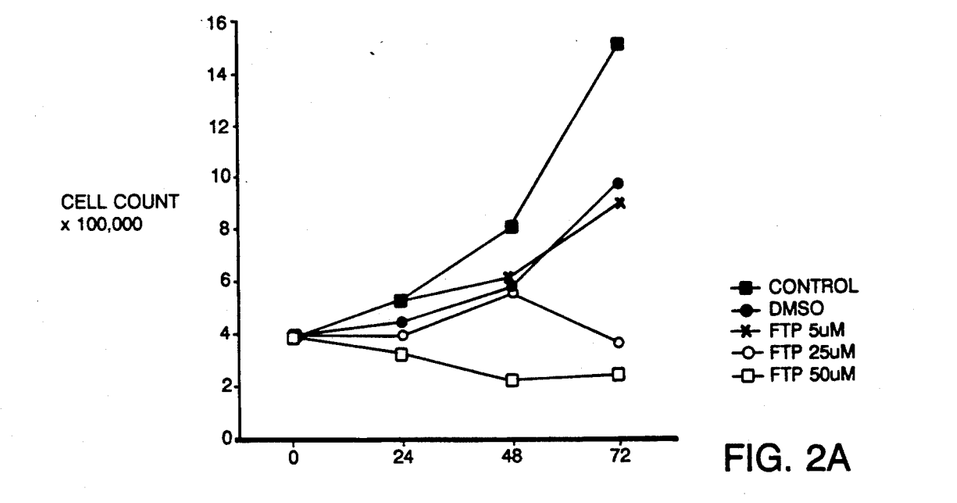
FIG. 2A–2D are a set of graphs which illustrate the effect of various compounds on the proliferation of HL-60 cells. In panels 2A–2C time is in hours. In panel 2D time is in days.
Figure 2B:
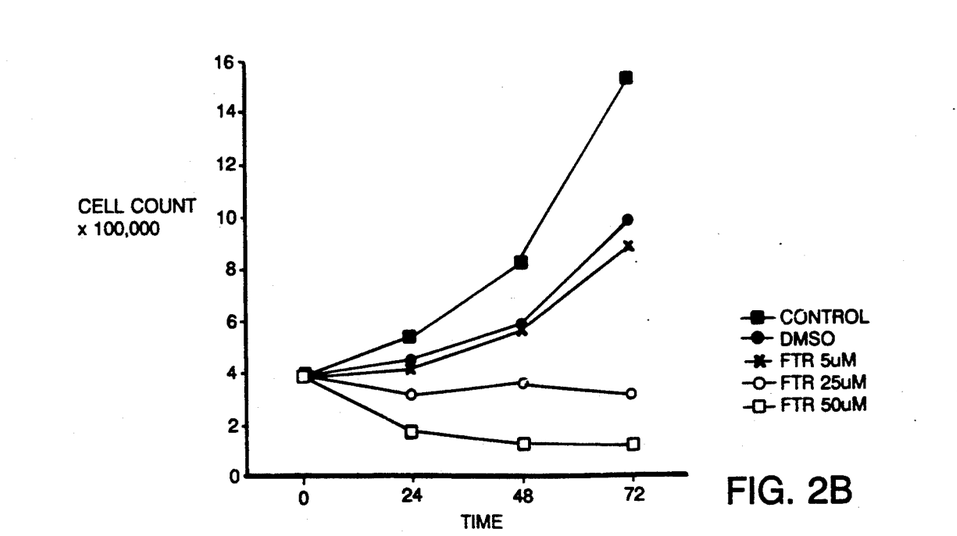
Figure 2C:
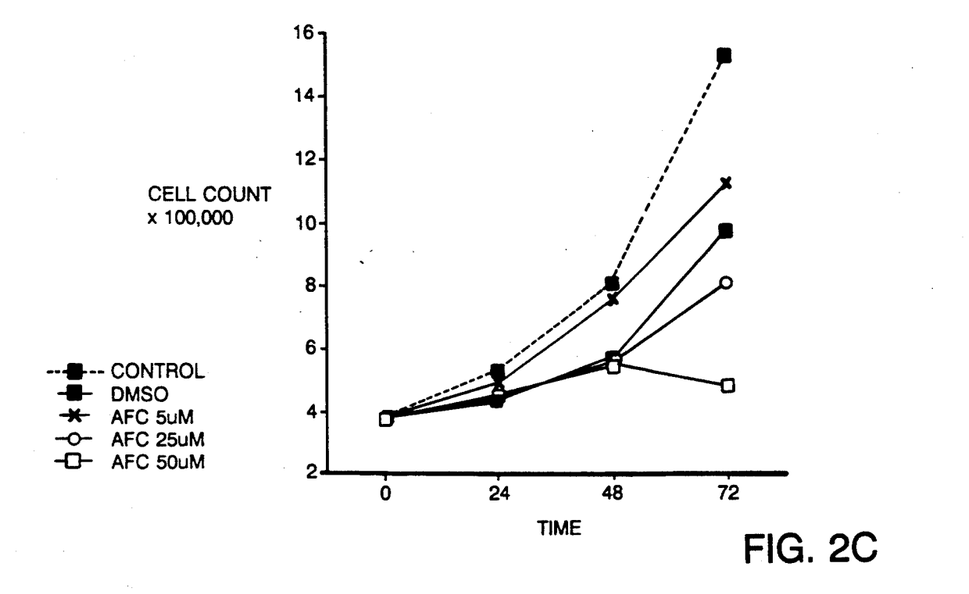
Figure 2D:
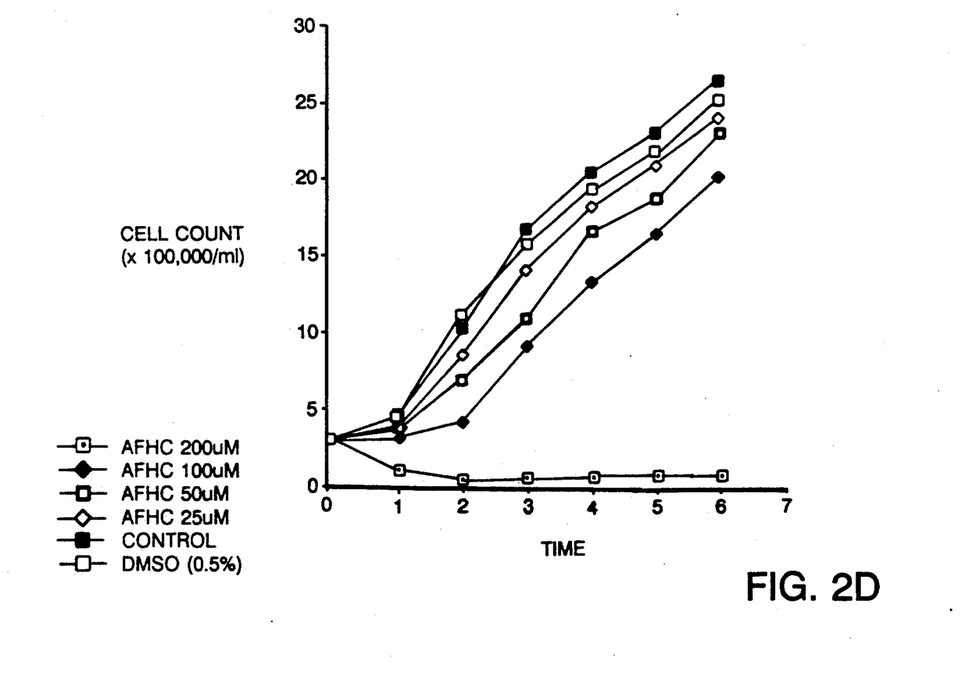

Referring to FIG. 1 which illustrates the structure of N-acetyl-S-farnesylcysteine (AFC), the following structural guidelines are useful for designing the compounds of the invention.

1. Substitutions at the 3 carbon of AFC and its derivatives produces an inhibitor.
2. Elimination of the 2 carbon or the 3 carbon of AFC produces a competitive inhibitor.
3. Changing the bond between the 2 carbon and the 3 carbon to a double bond produces an inhibitor.
4. Reduction of the farnesyl group produces an inhibitor.
5. The C2 carbon can accept a number of different substituents which are compatible with substrate activity; a peptide bond is not required at this position.

The design of the compounds of the invention is based on a knowledge of the structural requirements for recognition by methyltransferase. Recognition is indicated either by enzymatic action on the compound as a substrate or by enzyme inhibition. The structure of substrates provides a basis for inhibitor design as illustrated below.

The simple modified amino acid N-acetyl-5-farnesyl-L-cysteine (AFC) acts as a substrate for a methyltransferase capable of methylating a protein having a carboxyl-terminal —CAAX motif, ROS methyltransferase. This indicates that the polypeptide sequence of the natural protein substrates is not essential for substrate recognition. In fact, a peptide bond is not required for substrate recognition; substitution of the N-acetyl moiety of AFC by hydrogen creates S-farnesylthio-propionic acid (FTP) which is also a substrate for methyltransferase.

Analysis of AFC and FTP derivatives provides guidance for the design of methyltransferase inhibitors. For example, referring to FIG. 1, substitution of other groups for the N-acetyl group at carbon 2 in AFC generally results in the creation of a substrate, but substitution at the 3 carbon generally leads to the creation of a competitive inhibitor. Substitution of other groups for the carboxyl group in AFC generally interferes with substrate activity. The distance between the carbon of the carboxyl group and the sulfur is important; elimination of the 3 carbon or the presence of a double bond between the 2 carbon and the 3 carbon generates a competitive inhibitor. The farnesyl group is also important; reduced farnesyl groups and reduced geranylgeranyl groups are generally not active as substrates. This analysis provides guidance for the design of molecules capable of interfering with the methylation of proteins having a —CAAX motif. These guidelines are not meant to limit the invention to the specific above-described compounds.

While it appears that compounds which interfere with ras activity by interfering with methylation, other effects of these compounds may be physiologically important. For example, the inhibitors of the invention may bind or otherwise interfere with a membrane-localized ras receptor. Regardless of the exact mechanism of inhibitor action, the structures outlined are necessary and sufficient for interfering with ras function and thus for inhibiting ras dependent neoplastic growth. Further, the compounds of the invention can interfere with methylation of other proteins having a carboxyl-terminal —CAAX motif, for example, lamin B or various ras-related proteins. Such proteins may, like ras, play a role in cell proliferation.

Methylation of Transducin

Retinal transducin is a heterotrimeric signal transducing G protein whose $\gamma$ subunit (T$\gamma$) is farnesylated at cysteine (Lai et al., Proc. Natl. Acad. Sci. USA 87:7673, 1990). The farnesylcysteine residue is also methylated (Fukada et al., Nature 346:658, 1990).

We have identified an S-adenosyl-L-methionine-dependent methyltransferase activity in bovine retinal rod outer segments (ROS) which methylates the free carboxyl group of the farnesylated cysteine of bovine retinal transducin $\gamma$ subunit. The bovine retinal transducin $\gamma$ subunit has a carboxyl-terminal —CAAX motif and undergoes a farnesylation reaction similar to that observed on ras (Lai et al., Proc. Natl. Acad. Sci. USA 87:7673, 1990; Fukada et al., Nature 346:658, 1990). Bovine retinal rod outer segment S-adenosyl-L-methionine-dependent methyltransferase (ROS methyltransferase) provides a means by which to identify compounds capable of interfering with the methylation of proteins having a carboxyl-terminal —CAAX motif.

Preparation of ROS, Transducin, and Washed ROS Membranes

Frozen bovine retinas (Wanda Lawson Co., Lincoln, Nebr.) were used to prepare ROS membranes depleted of peripheral proteins using a modification of the procedure of Wessling-Resnick et al. (J. Biol. Chem. 262:3697, 1987). Briefly, ROS membranes were washed with low ionic strength buffer and 100$\mu$M GTP, resuspended in 50 mM Hepes-Na (pH 7.4), 100 mM NaCl, 5 mM MgCl$_2$, 0.1 mM phenylmethylsulfonyl fluoride, 0.1 mM dithiothreitol (buffer A) and stored in small aliquots at −80° C. until used. Transducin was isolated by disrupting ROS membranes by passing the membranes through a narrow needle and washing the disrupted membranes in a series of centrifugation steps as described by Wessling-Resnick et al. (J. Biol. Chem. 262:3697, 1987). Finally transducin was eluted from the membranes with 100$\mu$M GTP. The transducin-enriched supernatant was concentrated using Centriprep (Amicon).

Synthesis of Substrate Analogs

N-Acetyl-S-trans,trans-Farnesyl-L-cysteine (AFC) was prepared from N-acetyl-L-cysteine and trans,trans-farnesyl bromide as described by Kamiya et al. (Agric. Biol. Chem. 43:363, 1979). AFC was treated with methanol and HCl to produce the methyl ester of AFC.

In Vitro Methylation Reactions

For initial studies, the reaction mixture contained 20 $\mu$Ci of S-adenosyl-[methyl-$^3$H] methionine ([$^3$H]SAM) (2.34 $\mu$M, Amersham) and an aliquot of ROS (120$\mu$g of total protein) or of washed ROS membranes (80$\mu$g of total protein) in 100 $\mu$l of buffer A. Purified transducin was added to this mixture to a concentration of 5 $\mu$M. AFC, N-acetylcysteine, or AFC methylester was added in 2 $\mu$l of dimethyl sulfoxide to give a final concentration of 20 $\mu$M, and the reaction was carried out at 37° C.

In Vitro Methylation of T$\gamma$

Incubation of bovine ROS with [$^3$H]SAM results in the radioactive labeling of polypeptides with apparent molecular masses of 88, 60, 23-29, and 6 kDa. The methylation of the 88-kDa protein ($\alpha$ subunit of retinal phosphodiesterase) and of the 23- to 29-kDa polypeptides has already been reported (Swanson et al., J. Biol. Chem. 258:10599, 1983; Ota et al., J. Biol. Chem. 264:12879, 1989). The 6-kDa polypeptide coincides with T$\gamma$ in SDS/polyacrylamide gels. Moreover, incubation of purified transducin with extensively washed ROS and [$^3$H]SAM results in the labeling of the 6-kDa polypeptide and the membrane-associated 23- to 29-kDa proteins. These latter proteins are likely the retinal analogs of the prenylated and carboxyl-methylated small G proteins observed in cultured cells (Maltese et al., J. Biol. Chem. 265:2148, 1990) and the 23-kDa G protein purified from brain (Yamane et al., J. Biol. Chem. 264:20100, 1989). This conclusion is based on our previous observation that they are prenylated (Lai et al., Proc. Natl. Acad. Sci. USA 87:7673, 1990), the fact that they are methylated, their molecular masses, and their ability to bind GTP on nitrocellulose membranes.

When the radioactively labeled 6-kDa protein was analyzed by HPLC, the radioactivity co-eluted with T$\gamma$. When the radioactive polypeptide was cleaved with V8 protease and analyzed by HPLC, two main peaks of radioactivity were detected, one at 3 min in the position expected for radioactive methanol, and a second peak at 42 min. Analysis of this peptide by Edman degradation gave the sequence Leu-Lys-Gly-Gly-Xaa, which corresponds to the carboxyl-terminal fragment of T$\gamma$, confirming that methylation occurs at the cysteine residue, as has been recently reported (Fukada et al., Nature 346:658, 1990).

The nature of the methylation process is described below. The methyltransferase activity present in ROS membrane was destroyed by heat and inhibited by two well-characterized inhibitors of SAM-dependent methyltransferases, SAH (Barber et al., J. Biol. Chem. 259:7115, 1984) and sinefungin (Pugh et al., J. Biol. Chem. 253:4075, 1978).

AFC reduced incorporation of label by [$^3$H]SAM into proteins. AFC also serves as a substrate for the methyltransferase, producing AFC[$^3$H]methyl ester. The identity of this product was confirmed by co-elution with authentic standard by TLC and HPLC criteria. The enzymatic methyltransferase activity towards AFC was, as expected, destroyed by heat and inhibited by SAH and sinefungin. The necessity of the farnesyl moiety for substrate activity was demonstrated by showing that N-acetylcysteine is not a substrate for the methyltransferase.

The Methylation is a Reversible Process

Incubation of non-radioactive AFC methyl ester with [$^3$H]SAM and washed ROS membranes resulted in a linear, time-dependent incorporation of radioactivity into AFC methyl ester for at least 2 hr. This result indicates that the methylation reaction is reversible. To study the demethylation process directly, AFC[$^3$H]methyl ester was incubated with ROS membranes in the presence of methylation inhibitors. The methyl ester was rapidly hydrolyzed by the demethylase activity in the membranes. Heating of the reaction sharply decreased activity, as is expected of an enzymatic activity. Under similar conditions, demethylation of Tγ and the putative small G protein (23-29 kDa) was also observed.

ROS Methyltransferase Substrates

The above-described S-adenosyl-L-methione-dependent methyltransferase of bovine rod outer segments provides a model for methyltransferases which modify proteins, such as ras, which have a carboxyl-terminal —CAAX motif. Since AFC can serve as a substrate for ROS transferase, local peptide structure is generally not required for enzyme interaction. Therefore compounds which interfere with methyltransferase activity may be relatively small.

Starting with AFC there are a number of structural aspects of AFC which can be varied to yield substrates and inhibitors. For example, changes might be made in the N-acetyl group, the farnesyl group, and the carboxyl group. The sulfur may be changed to a sulfoxide, the distance between the sulfur and the carbon of the carboxyl group might be altered by the addition or removal of carbon atoms or double bond formation, and substituents might be added to one or more of the carbons between the sulfur and the carbon of the carboxyl group.

Synthesis of Methyltransferase Substrates and Inhibitors

N-Acetylhomocysteine was prepared from homocysteine thiolacetone by N-acetylation with acetic anhydride followed by base hydrolysis. The farnesylated compounds, AFC, N-acetyl-S-farnesyl-homocysteine (AFHC), 3-farnesylthiopropionic acid (FTP) and S-farnesylthioacetic acid (FTA) were prepared from trans,-trans-farnesyl bromide and N-acetyl-L-cysteine, N-acetylhomocysteine, 3mercaptopropionic acid and mercaptoacetic acid, respectively, using a general procedure as described for the preparation of AFC. This procedure is a variation of the method of Kamiya et al. (*Agric. Biol. Chem.* 43:363, 1979). N-Acetyl-L-cysteine (1.0 g, 6 mM), guanidine carbonate (1.3 g, 7 mM) and trans,trans-farnesyl bromide (1.7 g, 6 mM) were dissolved in 75 ml of acetone and the resulting solution stirred overnight at room temperature. The solvent was evaporated under reduced pressure and the residue taken up in ethyl acetate, washed successively with 10% HCl and water, dried (Na$_2$SO$_4$) and concentrated to a small volume. Chromatography of this material of this material on a silica column eluting with ethyl acetate/methanol (4:1-1:2) gave AFC (1.48 g, 66%) as a colorless oil [NMR (300 MHz, CDCl$_3$) δ 1.54 (6 H, s), 1.61 (3 H, s), 1.62 (3 H, s), 1.8-2.1 (8 H, m), 2.0 (3 H, s), 2.86 (1 H, dd, J=14.5 Hz, J=6.0 Hz), 2.96 (1 H, dd, J=14.5 Hz, J=4.8 Hz), 3.12 (1 H, dd, J= 13.7 Hz, J=7.5 Hz), 3.15 (1 H, dd, J=13.7 Hz, J=7.8 Hz), 4.71 (1 H, dt, J=7.2 Hz, J=5.3 Hz), 5.03 (2 H, t, J =6.9 Hz), 5.15 (1 H, t, J=7.6 Hz), 6.44 (1 H, d, J=7.2 Hz). AFHC was obtained as a thick colorless oil [64%, NMR (300 MHz, CDCl$_3$) δ 1.59 (6 H, s), 1.65 (3 H, s), 1.67 (3 H, s), 1.9-2.2 (10 H, m), 2.01 (3 H, s), 2.53 (2 H, t, J=7.0 Hz), 3.15 (2 H, d, J=7.8 Hz), 4.60 (1 H, m), 5.05 (2 H, m), 5.19 (1 H, t, J=7.8 Hz), 6.48 (1 H, d, J=8.0 Hz)], FTP was a colorless oil [68%, NMR (300 MHz, CDCl$_3$) δ 1.58 (6 H, s), 1.65 (3 H, s), 1.67 (3 H, s), 1.9-2.2 (8 H, m), 2.62 (2 H, t, J=5.7 Hz), 2.72 (2 H, t, J=5.7 Hz), 3.17 (2 H, d, J=8.5 Hz), 5.05 (2 H, m), 5.22 (1 H, t, J=8.5 Hz)] and FTA was a colorless oil [72%, NMR (300 MHz, CDCl$_3$) δ 1.58 (6 H, s), 1.64 (3 H, s), 1.66 (3 H, s), 1.9-2.2 (8 H, m), 3.19 (2 H, s), 3.28 (2 H, d, J=7.8 Hz), 5.06 (2 H, bt, J=5.2 Hz), 5.19 (1 H, J=7.8 Hz)]. N-acetyl-S-geranyl-L-cysteine (AGC) was obtained as a colorless oil [69%, NMR (300 MHz, CDCl$_3$) δ 1.54 (3 H, s), 1.60 (3 H, s), 1.62 (3 H, s), 2.01 (3 H, s), 2.10 (4 H, bs), 2.86 (1 H, dd, J=6.8 Hz, J=13.1 Hz), 2.95 (1 H, dd, J=5.5 Hz, J=13.1 Hz), 3.14 (2 H, m), 4.72 (1 H, m), 5.02 (1 H, m), 5.15 (1 H, t, J =6.8 Hz), 6.56 (1 H, d, J=6.9 Hz)] and was prepared by the method described above from geranyl bromide and N-acetyl-L-cysteine. The sulfoxide derivative, N-acetyl-S-farnesyl-sulfoxide (AFCS) [1:1 mixture of diastereomers, thick colorless oil, 87%, NMR (300 MHz, d$_6$-DMSO) δ 1.50 (6 H, s), 1.57 (6 H, s), 1.61 (6 H, s), 1.80 (6 H, s), 1.9-2.2 (16 H, m), 2.00 (6 H, s), 2.84 (1 H, dd, J=8.0 Hz, J= 15.9 Hz), 2.95 (1 H, d, J=14.5 Hz), 3.00 (1H, d, J= 14.5 Hz), 3.15 (1 H, dd, J=5.0 Hz, J=15.9 Hz), 3.4-3.6 (4 H, m), 4.39 (1 H, m), 4.53 (1 H, m), 5.05 (4 H, m), 5.20 (2 H, m), 8.34 (1 H, d, J=7.9 Hz), 8.43 (1 H, d, J=7.2 Hz)] was obtained by treating AFC with sodium periodate (1.2 mole equivalents) in methanol at 0° C., overnight. The methyl esters of the prenylated analogs were obtained from their parent carboxylic acids by treatment with methanolic HCl (0.05-1.0M). The methyl esters of all the analogs gave essentially identical NMR spectra to the analogs themselves except for singlet resonances, equivalent to 3 protons, at δ 3.74 for the methyl esters of AFC, ATC and AGC, at δ 3.74 and 3.76 for the diastereomers of the methyl ester of AFCS, at δ 3.48 for the methyl ester of AFHC, and at δ 3.68 for the methyl esters of FTP and FTA. The saturated derivative of ATC, N-acetyl-S-(3,7,11-trimethyldodecanyl)-L-cysteine [colorless oil, 76%, NMR (300 MHz, CDCl$_3$) δ 0.82 (3 H, d, J =6.8 Hz), 0.85 (9 H, d, J=6.7 Hz), 0.9-1.7 (17 H, m), 2.08 (3 H, s), 2.53 (2 H, m), 3.02 (2 H, d, J=5.8 Hz), 4.64 (1 H, bs), 4.74 (1 H, q, J=5.8 Hz), 6.42 (1 H, d, J= 5.8 Hz) was prepared by hydrogenation of AFC methyl ester in ethanol with palladium followed by saponification.

2-methyl-3-farnesylthiopropionic acid 1-thiofarnesane (TF) was dissolved in dry methanol along with 0.1 equivalent of Na in a dry flask under nitrogen. 1.5 equivalents of methyl-2-methylacrylate was added in methanol over 10 min with stirring. The reaction mixture was stirred for an additional hour and neutralized with dilute HCl. After evaporation, the product was applied to a preparative thin layer chromatographic plate and eluted with hexane/ethyl acetate. The pure product was removed from the plate and eluted with methanol. Yields were in the range of 50-75%. The product showed the anticipated nmr and infrared spectra. The parent acid was prepared from the ester by addition of one equivalent of sodium hydroxide in methanol. The product showed the anticipated nmr and infrared spectra.

3-methyl-3-farnesylthiopropionic acid

TF was dissolved in dry methanol along with 0.1 equivalent of Na all in a dry flask under nitrogen. 1.5 equivalents of methyl of methyl crotonate was added in methanol over 10 min with stirring. The reaction mixture was stirred was stirred for an additional hour and neutralized with dilute HCl. After evaporation, the product was applied to a preparative thin layer chromatography plate and eluted with hexane/ethyl acetate. The pure product was removed from the plate and eluted with methanol. The product showed the anticipated nmr and infrared spectra. The parent acid was prepared from the ester by addition of one equivalent of sodium hydroxide in methanol. The product showed the anticipated nmr and infrared spectra.

3-farnesyltio-trans-acrylic acid and 3-farnesyltio-cis-acrylic acid

TF was dissolved in dry methanol along with 0.1 equivalent of Na all in a dry flask under nitrogen. 1.5 equivalents of methyl propiolate was added in methanol of 10 min with stirring. The reaction mixture was stirred for and additional hour and neutralized with dilute HCl. After evaporation, the product was applied to a preparative thin layer chromatography plate and eluted with hexane/ethyl acetate. The cis and trans products were separated by HPLC. In methanol the ratio of cis to trans was approximately 7:1. A larger amount of trans isomer can be prepared photochemically form the cis isomer or by carrying out the reaction in tetrahydrofuran with trimethylamine as the base. The pure product was removed from the plate and eluted with methanol. The product showed the anticipated nmr and infrared spectra. The parent acid was prepared from the ester by addition of one equivalent of sodium hydroxide in methanol. The product showed the anticipated nmr and infrared spectra.

3-farnesylthiopropionamide

TF was dissolved in dry methanol along with 0.1 equivalent of Na all in a dry flask under nitrogen. 1.5 equivalents of acrylamide was added in methanol over 10 min with stirring. The reaction mixture was stirred for and additional hour and neutralized with dilute HCl. After evaporation, the product was applied to a preparative thin layer chromatography plate and eluted with hexane/ethyl acetate. The excess acrylamide was removed by water extraction. The pure product was removed from the plate and eluted with methanol. Yields were in the range of 50-75%. The product showed the anticipated nmr and infrared spectra.

3-farnesylthiopropionitrile

TF was dissolved in dry methanol along with 0.1 equivalent of Na all in a dry flask under nitrogen. 1.5 equivalents of acrylonitrile was added in methanol over 10 min with stirring. The reaction mixture was stirred for and additional hour and neutralized with dilute HCl. After evaporation, the product was applied to a preparative thin layer chromatography plate and eluted with hexane/ethyl acetate. The pure product was removed from the plate and eluted with methanol. Yields were in the range of 50-75%. The product showed the anticipated nmr and infrared spectra.

3-farnesylthio-2-methylenepropionic acid

TF was dissolved in dry methanol along with 0.1 equivalent of Na all in a dry flask under nitrogen. 1.5 equivalents of methyl-α-bromo-methylacrylate was added in methanol over 10 min with stirring. After evaporation, the product was applied to a preparative thin layer chromatography plate and eluted with hexane/ethyl acetate. The pure product was removed from the plate and eluted with methanol. The methyl ester was hydrolysed using Ktoms. Yields were in the range of 50-75%. The product showed the anticipated nmr and infrared spectra.

N-benzoyl-S-farnesylcysteine

S-farnesylcysteine was dissolved in dry ethyl acetate/triethylamine in a dry flask under nitrogen. equivalents of benzoylchloride was added in the cold and the suspension was allowed to stir for an hour. The solution was neutralized with dilute HCl. After evaporation, the product was applied to a preparative thin layer chromatography plate and eluted with hexane/ethyl acetate. The pure product was removed from the plate and eluted with methanol. Yields were in the range of 50-75%. The product showed the anticipated nmr and infrared spectra. The parent acid was prepared from the ester by the addition of one equivalent of sodium hydroxide in methanol. The product showed the expected nmr and infrared spectra.

N-bromoacetylfarnseylcysteine was prepared in an identical manner.

3-farnesyloxypropionic acid

All-trans-farnesol was reacted with methyl acrylate in the presence of one equivalent of 0.1 equivalent of potassium-tert butoxide/tetrahydorfuran/t-butanol for three hours at room temperature. The solution was acidified with 0.1N HCl, evaporated to dryness, and purified by thin layer chromatography on silica. The free acid was prepared by treatment of the ester with potassium hydroxide in methanol. The product showed the anticipated nmr and infrared spectra.

N-acetyl-Se-farnesyl-D,L-cysteine

N-acetylselenocysteine methyl ester was reacted with farnesylbromide identically as in the formation of AFC to produce the seleno derivative.

3-farnesylselenopropionic acid 1-selenofarnesare was prepared by reacting all-trans-farnesylbromide with selenourea followed by sodium hydroxide treatment. The salinofarnesane was reacted with methyl acrylate in tetrahydrofuran and triethylamine to produce the methyl ester product. The solution was acidified with 0.1N HCl, evaporated to dryness, and purified by thin layer chromatography on silica. The free acid was prepared by treatment of the ester with potassium hydroxide in methanol. The products showed the anticipated nmr and infrared spectra.

Other compounds according to the invention may be synthesized in a manner similar to that described above using standard techniques of organic chemistry. The compounds required for synthesis of the compounds of the invnetion may be obtained from Pierce, Aldrich, Fluka and Avanti (Birmingham, Ala.).

Analysis of Analogs

The above-described methyltransferase assay was used to analyze the analogs described above.

With AFC (Table 1) as a substrate for ROS methyl, a $K_M$ of 23 μM for methylation was measured utilizing ROS membranes as the source of methyltransferase enzyme. The apparent $K_M$ for AdoMet in this system is 2 μM, and the optimum pH for the enzyme is approximately 8.0. The $K_M$ with AFC as substrate is in the range of what has been determined for the methylation of synthetic peptides derived from ras proteins in other systems (Stephenson et al., *J. Biol. Chem.* 265:16248, 1990). This confirms that the peptide portion of the protein is generally unimportant for recognition by the methyl-transferase.

TABLE 1

Methyltransferase Substrates and Inhibitors

| STRUCTURE | NAME | Km | Ki |
|---|---|---|---|
| Far-S-CH2-CH(NHCOCH3)-C(=O)-OH | N-acetyl-S-farnesylcysteine | | 23 μM |
| Far-S-CH2-CH2-C(=O)-OH | 3-farnesylthiopropionic acid | | 14 μM |
| Far-S-CH2-C(=O)-OH | 2-farnesylthioacetic acid | | 4.6 μM |
| Far-S-CH2-CH2-CH(NHCOCH3)-C(=O)-OH | N-acetyl-S-farnesylhomocysteine | | 36.3 μM |
| Far-S(=O)-CH2-CH(NHCOCH3)-C(=O)-OH | N-acetyl-S-oxo-farnesylcysteine | | 13.2 μM |
| Far-S-CH=CH-C(=O)-OH (trans) | 3-farnesylthio-trans-acrylic acid | | 37 μM |
| Far-S-CH=CH-C(=O)-OH (cis) | 3-farnesylthio-cis-acrylic acid | | 40 μM |
| Far-O-CH2-CH2-C(=O)-OH | 3-farnesyloxypropionic acid | 26 μM | |
| Far-S-CH(CH3)-CH2-C(=O)-OH | 3-farnesylthiobutyric acid | | 30-40 μM |
| Far-S(=O)2-CH2-C(=O)-OH | 2-farnesylthioacetic acid sulfoxide | | <10 μM |
| Far-S-CH2-CH2-C(=O)-NH2 | 3-farnesylthiopropionamide | | inhibitor |
| Far-S-CH2-CH(CH3)-C(=O)-OH | 2-methyl-3-farnesylthiopropionic acid | 21 μM | |
| Far-S-CH2-CH2-NO2 | 2-farnesylthio-1-nitroethane | | inhibitor |

TABLE 1-continued
Methyltransferase Substrates and Inhibitors

| STRUCTURE | NAME | Km | Ki |
|---|---|---|---|
| | 2-farnesylthio-S-methyl | | inhibitor |
| | 3-farnesylthio-2-methylpropionic | | inhibitor |
| | S-farnesylcysteine | | inhibitor |
| | N-acetylgeranylgeranylcysteine | substrate | |
| | 3-farnesylthio-2-nitropropane | | inhibitor |
| | 3-farnesylthio-2-methylenepropionic acid | substrate | |
| | N-benzoyl-S-farnesylcysteine | substrate | |
| | disodium 2-farnesylthioethyl phosphate | | inhibitor |
| | 3-farnesylthiopropionitrile | | inhibitor |
| | N-acetyl-Se-farnesyl-D,L-cysteine | 51 μM | |
| | N-acetyl-S-farnesyl-D-cysteine | 42 μM | |
| | 3-farnesylselenopropionic acid | | 29 μM |
| | N-acetyl-S-geranyl-L-cysteine | substrate | |
| | 3-farnesylthiononanoic acid | | inhibitor |

TABLE 1-continued

| | Methyltransferase Substrates and Inhibitors | | |
|---|---|---|---|
| STRUCTURE | NAME | Km | Ki |
|  | 3-farnesylthiocyclohexanecarboxylic acid | | inhibitor |

For the compounds depicted in this table "Far" means a farnesyl group, i.e., the moiety:

and "GerGer" means a geranylgeranyl group, i.e., the moiety:

In both instances the * indicates the carbon atom which is attached to the rest of the molecule illustrated. For simplicity carbons are, in most cases, simply indicated by the end of a line and by the junction of two lines which meet at an angle in conventional manner of drawing organic compounds. Thus a farnesyl group includes 15 carbons and a farnesyl group includes 10 carbons. Also in the conventional manner, hydrogens are generally not explicitly indicated. Km is indicated for substrates and Ki is indicated for conventional inhibitors. In some cases the compounds status as a substrate or conventional inhibitor is indicated in place of the value of Km or Ki.

AFCS, the diastereomeric sulfoxides of AFC, were not methylated even at 500 μM (Table 1). The lack of activity towards AFCS shows that substantial specificity is directed at the sulfur atom of the substrate. Interestingly, the S-farnesyl homocysteine analog (AFHC) was also not a substrate for the methyltransferase (Table 1). This indicates that distance between the sulfur (or in other derivatives the oxygen or selenium) atom and the carboxyl group is important for substrate activity.

That the farnesyl moiety is important is shown by the fact that N-acetyl-S-geranyl-L-cysteine (AGC) is an exceedingly weak substrate for the enzyme (Table 1). Moreover, the completely saturated farnesane (3,7,11-trimethyldodecyl) derivative (ATC) is inactive as a substrate. These experiments demonstrate that substantial specificity is directed at the farnesyl side chain as well as at the thiopropionate moiety.

S-farnesyl-3-thiopropionic acid (FTP), in which the acetyl amide moiety is absent, proved to be an active substrate, with a $K_M$ of 13.7μM (Table 1), which is actually lower than that of AFC. Thus the peptide bond is not required for methyltransferase activity, and enzymatic activity is essentially directed at the farnesyl thiopropionate moiety. Furthermore, when the distance between the sulfur atom and the carboxyl group was shortened, as in S-farnesyl-2-thioacetic acid (FTA), substrate activity was lost (Table 1). This result is consistent with the results observed for AFHC.

While FTA, AFHC and AFCS are not substrates, they are all potent competitive inhibitors of AFC methylation and hence can be used inhibit methyltransferase activity and block methylation of such proteins as ras. A $K_i$ of 4.6 μM was calculated for the inhibition of AFC methylation by FTA. A $K_i$ 30.2 μM was determined for AFHC using similar analysis. For AFCS the calculated $K_i$ was 11.6 μM. Micromolar concentrations of FTA (10 μM) also inhibited the in vitro carboxyl-methylation of transducin γ subunit by 70%, as determined by densitometry of the fluorographic exposures of SDS gels of ROS samples that had been incubated with S-adenosyl-[methyl-$^3$H]methionine (2.3 μM, 85 Ci/mmol) in the presence or absence of FTA.

The above results demonstrate that an extreme reduction in structural complexity of the natural methyltransferase substrate transducin still produces molecules capable of being recognized by the methylating enzyme.

Two specific features have which are important for recognition by methyltransferase are discussed below. The first is that an uncomplexed sulfur atom is preferred at a particular distance from a carboxyl group. An intact farnesyl is preferred for substantial substrate activity. This is illustrated by the lack of activity of the farnesane derivative (ATC) and the marginal activity of the geranyl derivative (AGC) (Table 1).

Assay for Inhibition of Cell Growth

FTA, FTP, AFHC and AFC were tested for their ability to inhibit cell growth as follows.

HL-60 cells (ATCC CCL 240, American Type Culture Collection, Rockville, Md.) which harbor an activated ras gene were grown in RPMI medium (Gibco/BRL, Bethesda, Md.) supplemented with 10–15% fetal calf serum, L-glutamine, penicillin and streptomycin. These cells were treated with various concentrations of FTA, FTP, AFHC, or AFC dissolved in dimethyl sulfoxide (DMSO) or with DMSO only (In all experiments the final DMSO concentration was 1% or less). Treated ans untreated cells were incubated under standard culture conditions for several days. Cells were counted manually at 24 hour intervals using a trypan blue dye exclusion assay which counts only live, intact cells.

As shown in FIG. 2, FTP (panel A), FTA (panel B), AFC (panel C), and AFHC (panel D) can inhibit proliferation of HL-60 cells.

This assay can be used to screen newly created compounds.

Methyltransferase Activity in HL-60 Cells

In an in vitro labelling reaction similar to that described above for ROS membranes, the 23 kDa ras protein was the principle protein methylated by [$^3$H]SAM labelling of disrupted HL-60 cells. In this assay 50 μM FTA inhibited methylation of the 23 kDa protein by 61%. This demonstrates that FTA can specifically inhibit methylation of ras. AFC can be methylated by an activity present in the membrane of HL-60 cells, and this activity can be inhibited 90% by a 10-fold excess of FTA. AFC methyl ester can be turned over by HL-60 cell extracts demonstrating that the methylation reaction is reversible in HL-60 cell extracts. Finally, the γ subunit of transducin can be methylated by the methyltransferase present in HL-60 cell extracts.

Use

The compounds of the invention can be administered in an effective amount either alone or in combination with a pharmaceutically acceptable carrier or diluent. The compounds or compositions can be administered alone or in combination with other therapeutic agents.

The compounds of the invention may be administered by any convenient means, e.g., intravenously, orally, intramuscularly, or intranasally. Prolonged release systems, specifically at the site of a tumor, may be used.

I claim:

1. A compound of the formula
W-Y-Q-Z or W-Y-Z wherein W is a farnesyl group, a geranyl group, a geranylgeranyl group, a substituted farnesyl group or a substituted geranylgeranyl group;

wherein n = 1, 2, 3, 4, 5, or 6; each of $T_1'$... $T_n'$ and $T_1''$... $T_n''$ is independently: H, Fl, Br, —NHCOCH$_3$, —NH$_2$, a peptide, an alkane group, an alkene group, an polyethyleneglycol group, a saturated fatty acid, an unsaturated fatty acid, a monosaccharide, or a disaccharide; and Z is —COOH or salts or esters thereof, —CONH$_2$, —NO$_2$, —PO$_3$ or salts or esters thereof, —C≡N, or —SO$_3$ or salts or esters thereof, provided that when W is farnesyl, Y is —S—, n=2, and either $T_2'$ or $T_2''$ is —NHCOCH$_3$, then Z is not —COOH. said compound being characterized by interfering with enzymatic methylation of a peptide having the carboxyl-terminal motif —CAAX wherein C=cysteine, A=aliphatic amino acid, and X=any amino acid.

2. The compound of claim 1 wherein W is a farnesyl group, a geranyl group, or a geranylgeranyl group; Z is —COOH; Y is —S—, and n=1, 2 or 3.

3. The compound of claim 1 wherein n=1.

4. A therapeutic composition comprising the compound of claim 1 in a pharmaceutically acceptable carrier.

5. The compound of claim 1 said peptide being the γ subunit of transducin.

6. The compound of claim 2, said compound being N-acetyl-S-farnesylcysteine, 3-farnesylthiopropionic acid, 2-farnesylthioacetic acid, N-acetyl-S-farnesylhomocysteine, 3-farnesylthio-trans-acrylic acid, 3-farnesylthio-cis-acrylic acid, 3-farnesylthiobutyric acid, 21-methyl-3-farnesylthiopropionic acid, S-farnesylcysteine, 3-farnesylthio-2-methylenepropionic acid, N-benzoyl-S-farnesylcysteine, N-acetyl-S-farnesyl-D-cysteine, 3-farnesylthiononanoic acid, N-acetylgeranylgeranylcysteine, or N-acetyl-S-geranyl-L-cysteine.

7. The compound of claim 1 wherein W is a farnesyl group; Y is Se; n is 1 or 2; and Z is —COOH.

8. The compound of claim 7 wherein said compound is N-acetyl-Se-farnesyl-D,L-cysteine or 3-farnesylselenopropionic acid.

9. The compound of claim 1 wherein Y is S=O.

10. The compound of claim 9, said compound being 2-farnesylthioacetic acid or N-acetyl-S-oxo-farnesylcysteine.

11. The compound of claim 1 wherein said compound is 3-farnesyloxypropionic acid.

12. The compound of claim 1 wherein said compound is 3-farnesylthiopropionamide.

13. The compound of claim 1, wherein said compound is 2-farnesylthio-1-nitroethane.

14. The compound of claim 1 wherein said compound 2-farnesylthio-S-methyl acetothiohydroximate.

15. The compound of claim 1 wherein said compound 3-farnesylthio-2-methylenepropionic methyl ester.

16. The compound of claim 1 wherein said compound is 3-farnesylthio-2-nitropropane.

17. The compound of claim 1 wherein said compound is disodium 2-farnesylthioethyl phosphate.

18. The compound of claim 1 wherein said compound is 3-farnesylthiopropionitrile.

19. The compound of claim 1 wherein said compound is 3-farnesylthiocyclohexane carboxylic acid.

20. The compound of claim 1 wherein said compound is 2-farnesylthioacetic acid.

21. The compound of claim 1 wherein W is a farnesyl group, a geranyl group, or a geranylgeranyl group; y is —S—, —O—, or —Se—; and n=1, 2, or 3.

22. The compound of claim 1 wherein said compound is N-acetyl-S-farnesylcystein, 3-farnesylhomocysteine, N-acetyl-S-oxo-farnesylcysteine, 3-farnesylthio-trans-acrylic acid, 3-farnesylthio-cis-acrylic acid, 3-farnesyloxypropionic acid, 3-farnesylthiobutyric acid, 2-farnesylthioacetic acid sulfoxide, 3-farnesylthiopropionamide, 2-methyl-3-farnestylthiopropionic acid, 2-farnesylthio-1-nitroethane, 2-farnesylthio-S-methyl acetothiohydroximate, 3-farnesylthio-2-methylenepropionic methyl ester, S-farnesylcysteine, N-acetylgeranylgeranylcysteine, 3-farnesylthio-2-nitropropane, 3-farnesylthio-2-methylenepropionic acid, N-benzoyl-S-farnesylcysteine, disodium 2-farnesylthioethyl phosphate, 3-farnesylthiopropionitrile N-acetyl-Se-farnesyl-D,L-cysteine, N-acetyl-S-farnesyl-D-cysteine, 3-farnesylselenopropionic acid, N-acetyl-S-geranyl-L-cysteine, 3-farnesylthiononanoic acid, or 3-farnesylthiocyclohexanecarboxylic acid.

* * * * *

UNITED STATES PATENT AND TRADEMARK OFFICE
CERTIFICATE OF CORRECTION

PATENT NO. : 5,202,456

DATED : April 13, 1993

INVENTOR(S) : Robert R. Rando

It is certified that error appears in the above-indentified patent and that said Letters Patent is hereby corrected as shown below:

At column 10, lines 18, insert --1.1-- before "equiva-".

At column 13, line 1, insert --acetothiohydroximate-- after "methyl".

At column 13, line 10, insert --methyl ester-- after "methylpropionic".

At column 17, line 11, insert new paragraph after --ras.--.

At column 18, line 10, replace "21" with --2--.

UNITED STATES PATENT AND TRADEMARK OFFICE
CERTIFICATE OF CORRECTION

PATENT NO. : 5,202,456

DATED : April 13, 1993

INVENTOR(S) : Robert R. Rando

It is certified that error appears in the above-indentified patent and that said Letters Patent is hereby corrected as shown below:

--25. The compound of claim 1 wherein said compound is N-acetyl-S-farnesylcysteine, 3-farnesylthiopropionic acid, 2-farnesylthioacetic acid, N-acetyl-S-farnesylhomocysteine, N-acetyl-S-oxo-farnesylcysteine, 3-farnesylthio-trans-acrylic acid, 3-farnesylthio-cis-acrylic acid, 3-farnesyloxypropionic acid, 3-farnesylthiobutyric acid, 2-farnesylthioacetic acid sulfoxide, 3-farnesylthiopropionamide, 2-methyl-3-farnesylthiopropionic acid, 2-farnesylthio-1-nitroethane, 2-farnesylthio-S-methyl acetothiohydroximate, 3-farnesylthio-2-methylenepropionic methyl ester, S-farnesylcysteine, N-acetylgeranylgeranylcysteine, 3-farnesylthio-2-nitropropane, 3-farnesylthio-2-methylenepropionic acid, N-benzoyl-S-farnesylcysteine, disodium 2-farnesylthioethyl phosphate, 3farnesylthiopropionitrile N-acetyl-Se-farnesyl-D,L-cysteine, N-acetyl-S-farnesyl-D-cysteine, 3-farnesylselenopropionic acid, N-acetyl-S-geranyl-L-cysteine, 3-farnesylthiononanoic acid, or 3-farnesylthiocyclohexanecarboxylic acid.--

Signed and Sealed this

Nineteenth Day of July, 1994

Attest:

BRUCE LEHMAN

Attesting Officer

Commissioner of Patents and Trademarks